(12) United States Patent
Topping et al.

(10) Patent No.: US 11,885,482 B2
(45) Date of Patent: Jan. 30, 2024

(54) LUMINAIRE AND ILLUMINATION SYSTEM

(71) Applicant: SKYJOY LIMITED, Belfast (GB)

(72) Inventors: Pamela Topping, Belfast (GB); Lloyd Crawford, Belfast (GB)

(73) Assignee: SKYJOY LIMITED, Belfast (GB)

( * ) Notice: Subject to any disclaimer, the term of this patent is extended or adjusted under 35 U.S.C. 154(b) by 0 days.

(21) Appl. No.: 17/766,964

(22) PCT Filed: Oct. 9, 2020

(86) PCT No.: PCT/GB2020/052513
§ 371 (c)(1),
(2) Date: Apr. 6, 2022

(87) PCT Pub. No.: WO2021/069914
PCT Pub. Date: Apr. 15, 2021

(65) Prior Publication Data
US 2023/0151955 A1 May 18, 2023

(30) Foreign Application Priority Data
Oct. 9, 2019 (GB) ...................................... 1914607

(51) Int. Cl.
*F21V 23/04* (2006.01)
*F21V 3/06* (2018.01)
*A61N 5/06* (2006.01)
*F21Y 105/18* (2016.01)
*F21Y 113/13* (2016.01)
(Continued)

(52) U.S. Cl.
CPC ........ *F21V 23/0442* (2013.01); *A61N 5/0618* (2013.01); *F21V 3/0625* (2018.02); *F21V 23/0435* (2013.01); *A61N 2005/0626* (2013.01); *A61N 2005/0652* (2013.01); *A61N 2005/0663* (2013.01); *F21W 2131/208* (2013.01); *F21Y 2105/18* (2016.08); *F21Y 2113/13* (2016.08); *F21Y 2115/10* (2016.08)

(58) Field of Classification Search
CPC ............... F21V 23/0442; F21V 3/0625; F21V 23/0435; F21V 21/03; F21V 21/02; A61N 5/0618; A61N 2005/0626; A61N 2005/0652; A61N 2005/0663; F21Y 2105/18; F21Y 2113/13; F21Y 2115/10; F21W 2131/208
See application file for complete search history.

(56) References Cited

U.S. PATENT DOCUMENTS 10,100,987 B1 * 10/2018 Dell'Ario .............. H05B 47/16
2004/0105264 A1 * 6/2004 Spero .................. F21V 23/0471
362/276
(Continued)

FOREIGN PATENT DOCUMENTS

WO 2012146256 A2 11/2012

OTHER PUBLICATIONS

Apr. 13, 2023—(GB) Examination Report—App. No. 2204846.6.
(Continued)

*Primary Examiner* — Bao Q Truong
(74) *Attorney, Agent, or Firm* — Banner & Witcoff, Ltd.

(57) ABSTRACT

A luminaire (11) is provided having sensors means (16) for detecting or determining information relating to a subject. The information is usable to determine changes to light output.

18 Claims, 2 Drawing Sheets

(51) Int. Cl.
*F21Y 115/10* (2016.01)
*F21W 131/208* (2006.01)

(56) References Cited

U.S. PATENT DOCUMENTS

| | | | |
|---|---|---|---|
| 2006/0002110 A1* | 1/2006 | Dowling | F21V 23/005 |
| | | | 362/249.05 |
| 2010/0277316 A1* | 11/2010 | Schlangen | F21S 10/02 |
| | | | 315/312 |
| 2011/0084614 A1 | 4/2011 | Eisele et al. | |
| 2015/0062892 A1 | 3/2015 | Krames et al. | |
| 2016/0054023 A1 | 2/2016 | Baker et al. | |
| 2016/0128158 A1 | 5/2016 | Harder | |
| 2016/0286616 A1 | 9/2016 | van de Ven | |
| 2017/0105265 A1 | 4/2017 | Sadwick | |
| 2018/0168020 A1 | 6/2018 | Casey et al. | |
| 2019/0041030 A1* | 2/2019 | Dahlen | F21V 15/01 |
| 2019/0136618 A1 | 5/2019 | Hebeisen et al. | |
| 2019/0242539 A1 | 8/2019 | Roberts | |
| 2019/0297704 A1 | 9/2019 | van de Ven et al. | |

OTHER PUBLICATIONS

Aug. 11, 2022—(GB)—Examination Report—App. No. GB1914607.5.
Oct. 7, 2022—(GB) Examiner's Report—App. No. GB22404846.6.
Dec. 16, 2020—(WO) International Search Report and Written Opinion—Appl. No. PCT/GB2020/052513.
Nov. 8, 2023—(EP) Examination Report—App. No. 20 801 352.4.
Nov. 2, 2023—(GB) Examination Report—App. No. 2204846.6.

* cited by examiner ing such. The present invention relates to an improved luminaire, and includes an improved illumination system incorporating at least one such luminaire.

LUMINAIRE AND ILLUMINATION SYSTEM

CROSS-REFERENCE TO RELATED APPLICATIONS

This application is a U.S. National Stage application under 35 U.S.C. § 371 of International Application PCT/GB2020/052513 (published as WO 2021/069914 A1), filed Oct. 9, 2020, which claims the benefit of priority to U.K. Application No. 1914607.5 filed Oct. 9, 2019. Each of these prior applications is hereby incorporated by reference in its entirety.

The present invention relates to an improved luminaire, and includes an improved illumination system incorporating at least one such luminaire.

As used in this specification the term "luminaire" will be understood to mean an illumination unit including at least one light source, a mount for holding the light source or sources, and a power supply for delivering power to the light source or sources. Usually, but not inevitably there would also be included some form of cosmetic covering or shade for diffusing or directing the light emitted by the light source or sources.

There are various circumstances in which it would be of benefit to be able to vary the illumination in a given environment, not only by varying the brightness or intensity of the illumination but also (or alternatively) by varying one or more of the other illumination parameters, such as, for example, the colour temperature of the light output.

One such requirement occurs in the illumination of hospital wards, asylums or prison cells, as well as in the rooms of sheltered accommodation, care homes, and nursing homes, which are very often occupied by the elderly or infirm, who have little or no opportunity to leave the environment, and where the ambient lighting is almost always entirely artificial. Such lighting almost always illuminates the environment in a fixed and unvarying manner, offering no indication of the diurnal variation of natural light. It is known, however, that the diurnal variation of natural light, both in terms of its intensity (brightness) and in terms of its colour temperature, has a significant effect on the circadian rhythms of individuals subject to such lighting, often leading to cognitive impairment and deterioration of health and well-being. Such deterioration shows itself in the increasing occurrence of age-related conditions such as vascular dementia and Alzheimer's disease. The care of people with these conditions is costing the economy very considerable sums and this is increasing all the time with the increase in population suffering such diseases. This can only get worse as the population at large ages.

The present invention seeks to provide a luminaire and a lighting system including such, which will at least to some extent mitigate, and even alleviate, the detrimental effects of artificial lighting, and provide, moreover, means by which the care of people affected by dementia and other such life-inhibiting conditions can be achieved in an economic manner, possibly requiring less intervention by care staff and promoting a sense of independence while at the same time slowing the onset of such cognitive impairment as is currently causing considerable concern at a socio-economic level. Use of luminaires made according to the present invention may well enrich the experience of living well with dementia and at the same time promote a healthy lifestyle.

The present invention also seeks to provide means by which it will be possible unobtrusively to monitor persons with cognitive impairment without negatively impacting on their sense of well-being and self.

Some aspects and embodiments may relate to biodynamic/circadian luminaires and/or LEDs.

Some aspects and embodiments may relate to networked (for example wirelessly networked) luminaires.

In some aspects and embodiments a device may be formed as a light fixture or a lighting fixture.

Some aspects and embodiments may relate to luminaires with occupancy sensors.

An aspect provides a luminaire having sensors means for detecting or determining information relating to a subject, in which the information is usable to determine changes to light output.

A lighting device having sensors means for detecting or determining information relating to a subject, in which the information is usable to determine changes to light output.

An aspect provides a luminaire having sensors means for detecting or determining one or more behaviours and/or psychological state/s of a subject, in which behaviour/s detected by the sensor means are usable to determine changes to light output.

Examples of information which may be collected/assessed/determined by or as a result of the sensor/s include: temperature, posture, Some embodiments may include a component of pre-programming. Some embodiments may include a component of learning.

Some aspects and embodiments may relate to psycho-physiology and/or psychology and/or physiology based/influence/determined/assessed inputs/output.

For example, some aspects and embodiments may seek to understand and/or act upon psychological states and processes by means of observing or measuring physiological changes (e.g., blushing indicates embarrassment, sweating is associated with fear, etc.).

Information such as the behaviour patterns detected by the sensor may be used to make changes to biodynamic light output such as intensity, colour or sequence of change in order to improve behavioural responses, enhance reduction in stress and/or anxiety and improve the beneficial effects of biodynamic light such as well-being and contentment.

Some embodiments include a feature of diurnal variation and/or seasonal variation.

An aspect provides a luminaire having sensors means for detecting behavioural (which may include biobehavioral) patterns of a subject, in which behaviour patterns detected by the sensor are usable to determine changes to biodynamic light output.

Light output changes may include, for example, intensity, colour or sequence of change.

The luminaire may have the capacity to update circadian performance based on data received from or by the sensor means.

An aspect provides a networkable circadian luminaire with sensor means, the luminaire has the capacity to update circadian performance based on data received from or by the sensor means.

A further aspect provides a biodynamic luminaire with sensor means, the luminaire has the capacity to update biodynamic illumination output based on data received from or by the sensor means.

A further aspect provides a luminaire having sensor means, the luminaire includes means for changing illumination output based on data received from or by the sensor means.

A further aspect provides a wirelessly networked biodynamic/circadian luminaire with an integral/replaceable sensor that tracks movement/body temperature or other signs and has the capacity to update its circadian performance based on the data received.

In some aspects and embodiments the term "luminaire" may be defined as: a complete lighting unit consisting of a lamp or lamps together with the parts designed to distribute the light, to position and protect the lamps, and to connect the lamps to the power supply.

Millimetre wave technology may be used, for example as a potential sensor technology. Millimeter wave (MM wave), also known as millimeter band, is the band of electromagnetic spectrum with wavelengths between 10 millimeters (30 GHz) and 1 millimeter (300 GHz). It enables higher data rates than at lower frequencies.

According to a further aspect of the present invention there is provided a luminaire having control means for varying the value of one or more of the properties of the output illumination, and sensor means for detecting at least one variable property of the illuminated environment, whereby to vary the output illumination of the luminaire in dependence on the detected value of the said sensed variable property.

In some embodiments one of the properties of the output illumination of the luminaire is the colour temperature. Alternatively or additionally one of the properties of the output illumination of the luminaire may be the light intensity. It is particularly intended within the scope of the present invention that at least one of the properties of the output illumination is varied in accordance with a predetermined programme.

It may be particularly convenient if the programme of variation of the said all least one property is replaceable or updateable by wireless means.

It is envisaged that in some embodiments of the invention the said at least one variable property of the illuminated environment is a property of an occupant within the illuminated environment. Preferably, the said variable property of the occupant of the illuminated environment includes the movement of the said occupant, and the luminaire includes means for detecting the movement of an occupant within the illuminated environment.

The luminaire of the invention may also include means for detecting the temperature of the illuminated environment and/or the temperature of an occupant within the illuminated environment. The means sensitive to a property of an occupant of the illuminated environment is conveniently operable to detect one of more of the occupant's pallor, eye movement, sleep pattern, and/or activity level.

In an embodiment of the invention the said control means is preliminarily programmed to vary the output illumination whereby to entrain the circadian rhythm of the body of an occupant within the illuminated environment. It is useful if the said means for varying the value of one or more of the properties of the output illumination includes means for storing a sequence of variation in the luminaire itself.

Typically, but not exclusively, the light source within the luminaire is one or more light-emitting diodes. There may, of course, be a plurality of sets of individual light sources of different properties, in which case the control means may selectively energise the light sources of different sets to achieve the target property of the output illumination.

Alternatively, or additionally, one of more of the properties of the output illumination can be varied remotely via a wireless mesh network. In another embodiment there are means for varying the programme of output variations via an electronic smartphone or tablet, typically using an App.

Conveniently, there may be an internal memory for storing an output variation sequence whereby to allow the luminaire to function independently of other such luminaires in the illuminated environment. It may also be particularly valuable for the luminaire and/or system of the invention to be provided with a clock, such as an external battery-operated clock that maintains the local time in the event of mains failure or an internal battery-operated clock, by means of which the programme of variation of the output illumination can be reset in the event of a power failure of the primary power supply. In some embodiments only one clock per mesh network is provided.

In some embodiments a clock device to maintain time keeping in the event of mains failure is a module on the network.

In order to maintain a sense of independence for the user there may also be provided a user-operable on/off switch operation of which does not, however, change the programme of variation of output illumination. This gives the user the ability to control his or her own environmental lighting without compromising the therapeutic functionality of the variations in illumination properties such as colour temperature and brightness so important for maintaining the important temporal relationship of the occupant's circadian rhythms with the actual time of day. For convenience the said user-operable on\off switch may be manually operable or operable via a wireless kinetic switch requiring no battery.

The said sensor may be operable to detect one or more variable environmental property including, but not limited to, the temperature, humidity, carbon dioxide level, carbon monoxide level, and ambient noise level, and/or one of more variable property of an occupant of the illuminated environment, including, but not limited to, movement of the occupant, body temperature, heart rate, skin colour (pallor) eye movement, and/or any stress level indicators relevant to that occupant in that environment.

The or each sensor may be removable and replaceable in a casing mount without requiring tools.

The sensor firmware may be updatable wirelessly.

For special situations, for example for use in prisons or other high risk or potentially hostile environments (such as use for the military) the luminaire of the invention may be encased in a vandal-proof or otherwise ruggedised casing.

A further aspect provides a lighting fitment comprising sensor means, in which the sensor means is operable to detect one or more variable environmental property including, but not limited to, the temperature, humidity, carbon dioxide level, carbon monoxide level, and ambient noise level, and/or one of more variable property of an occupant of an illuminated environment, including, but not limited to, movement of the occupant, body temperature, heart rate, skin colour (pallor) eye movement, and/or any stress level indicators relevant to an occupant in an environment.

The present invention also comprehends an illumination system comprising one or a plurality of luminaires and/or fitments as described hereinabove, and a remote processor in communication therewith and operable by way of an algorithm to prepare an indication of one or more of an occupant's movement, sleep pattern, or repetitive behaviour pattern indicative of the occupant's stress level, perceived anxiety level or the like. In such a system the said remote processor may be a processing centre including means to inform, alert, and/or contact supervisory staff in the event of the detection of predetermined or anomalous signals from one or more of the said sensors.

Data may be transmitted/received to/from/between the luminaire/s and/or sensor/s and/or remote processor/s (and/or between other components of a luminaire and/or illumination system).

Data may be transmitted/exchanged continuously. Alternatively or additionally, data may, for example, be transmitted periodically and/or contemporaneously with a change in status.

The transmission of data may be automatic.

In an example, data can be transmitted using a short-range wireless communications protocol such as: ANT, ANT+, Bluetooth, Bluetooth Low Energy, Cellular, IEEE 802.15.4, IEEE 802.22, ISA100a, Infrared, ISM Band, Near-Field Communications, RFID, 6LoWPAN, Ultra-Wideband, Wireless HART, WirelessHD, WirelessUSB, ZigBee, Z-Wave.

Data about the functioning of the luminaire/sensor/processor may, for example, be transmitted/stored for use, for example, by a clinician.

Data may be transmittable to a proxy for onward transmission. For example, data may be transmitted to an item of equipment such as a mobile phone, laptop computer or tablet. From there, some or all of the data may be available to the individual and/or may be onwardly transmitted to, for example, a web server. This then allows the data to be accessed, for example, by a clinician/warden/carer to analyse the individual. Because the present invention may allow for data to be transmitted regularly, the clinician could be kept informed about their patient on a regular basis, for example with constant, real-time, hourly, daily, weekly or monthly updates. The clinician may also have the ability to request and view real-time data.

Data may be storable locally on the device. This could be useful, for example, if data transfer is not possible.

Data may be encrypted for transmission from the device/system. In an example, the proxy can transmit the received data in encrypted form and may not have access to a decryption key. The data may be decrypted when accessed by, for example, a clinician/warden/carer as noted above.

Luminaires/light fixtures formed in accordance with the present invention may also have other features, such as reflectors for directing light, an aperture (with or without a lens), an outer shell or housing for output means (e.g. lamp) alignment and protection, an electrical ballast or power supply, and a shade to diffuse the light or direct it, for example towards a workspace (e.g., a desk lamp).

The present invention also provides an environment (e.g. a room or office) provided with one or more devices formed in accordance with the present invention.

The present invention also provides a method of monitoring a subject, comprising the provision of a luminaire having sensors means for detecting or determining information relating to a subject, in which the information is usable to determine changes to light output.

Further aspects and embodiments are provided in the following numbered list of paragraphs.

1. A luminaire having control means for varying the value of one or more of the properties of the output illumination, and sensor means for detecting at least one variable property of the illuminated environment, whereby to vary the output illumination of the luminaire in dependence on the detected value of the said sensed variable property.
2. A luminaire as claimed in paragraph 1, in which one of the properties of the output illumination of the luminaire is the colour temperature.
3. A luminaire as claimed in paragraph 1 or paragraph 2, in which one of the properties of the output illumination of the luminaire is the light intensity.
4. A luminaire as claimed in any of paragraphs 1 to 3, in which at least one of the properties of the output illumination is varied in accordance with a predetermined programme.
5. A luminaire as claimed in paragraph 4, in which the programme of variation of the said all least one property is replaceable or updatable by wireless means.
6. A luminaire as claimed in any preceding paragraph, in which the said at least one variable property of the illuminated environment is a property of an occupant within the illuminated environment.
7. A luminaire as claimed in paragraph 6, in which the property of the occupant of the illuminated environment includes the movement of the said occupant, and the luminaire includes means for detecting the movement of an occupant within the illuminated environment.
8. A luminaire as claimed in paragraph 6 or paragraph 7, including means for detecting the temperature of the illuminated environment and/or the temperature of an occupant within the illuminated environment.
9. A luminaire as claimed in any of paragraphs 6 to 8, in which the means sensitive to a property of an occupant of the illuminated environment is operable to detect one or more of the occupant's pallor, eye movement, sleep pattern, and/or activity level.
10. A luminaire as claimed in any preceding paragraph, in which the said control means is preliminarily programmed to vary the output illumination whereby to entrain the circadian rhythm of the body of an occupant within the illuminated environment.
11. A luminaire as claimed in any preceding paragraph, in which the said means for varying the value of one or more of the properties of the output illumination includes means for storing a sequence of variation in the luminaire itself.
12. A luminaire as claimed in any preceding paragraph, in which the light source within the luminaire is one or more light-emitting diodes.
13. A luminaire as claimed in any preceding paragraph, in which there are a plurality of sets of individual light sources of different properties, and the control means selectively energises the light sources of different sets to achieve the target property of the output illumination.
14. A luminaire as claimed in any preceding paragraph, in which one of more of the properties of the output illumination can be varied remotely via a wireless mesh network.
15. A luminaire as claimed in paragraph 14, in which there are means for varying the programme of output variations via an electronic smartphone or tablet, typically using an App.
16. A luminaire as claimed in any preceding paragraph, in which there is an internal memory for storing an output variation sequence whereby to allow the luminaire to function independently of other such luminaires in the illuminated environment.
17. A luminaire as claimed in any preceding paragraph, in which there is provided a clock by means of which the programme of variation of the output illumination can be reset in the event of a power failure of the primary power supply.

18. A luminaire as claimed in any preceding paragraph, in which there is provided a user-operable on/off switch operation of which does not, however, change the programme of variation of output illumination.
19. A luminaire as claimed in paragraph 18, in which the said user-operable on\off switch is manually operable or operable via a wireless kinetic switch requiring no battery.
20. A luminaire as claimed in any of paragraphs 1 to 19, in which the said sensor is operable to detect one or more variable environmental property including, but not limited to, the temperature, humidity, carbon dioxide level, carbon monoxide level, and ambient noise level, and/or one or more variable property of an occupant of the illuminated environment, including, but not limited to, movement of the occupant, body temperature, heart rate, skin colour (pallor) eye movement, and/or any stress level indicators relevant to that occupant in that environment.
21. A luminaire as claimed in any of paragraphs 1 to 20, in which the or each sensor is removable and replaceable in a casing mount without requiring tools.
22. A luminaire as claimed in any of paragraphs 1 to 21, in which the sensor firmware is updatable wirelessly.
23. A luminaire as claimed in any preceding paragraph, encased in a vandal-proof or otherwise ruggedised casing for use in potentially hostile environments.
24. An illumination system comprising one or a plurality of luminaires as claimed in any preceding Claim, and a remote processor in communication therewith and operable by way of an algorithm to prepare an indication of one or more of an occupant's movement, sleep pattern, or repetitive behaviour pattern indicative of the occupant's stress level, perceived anxiety level or the like.
25. An illumination system as claimed in paragraph 25, in which the said remote processor is a processing centre including means to inform, alert, and/or contact supervisory staff in the event of the detection of predetermined or anomalous signals from one or more of the said sensors.

Different aspects and embodiments can be used together or separately.

Embodiments of the present invention are more particularly described, by way of non-limiting example, below.

The example embodiments are shown in sufficient detail to enable those of ordinary skill in the art to embody and implement the systems and processes herein described. It is important to understand that embodiments can be provided in many alternate forms and should not be construed as limited to the examples set forth herein.

Embodiments can be modified in various ways and take on various alternative forms. There is no intent to limit to the particular forms disclosed. On the contrary, all modifications, equivalents, and alternatives falling within the scope of the appended claims should be included.

Unless otherwise defined, all terms (including technical and scientific terms) used herein are to be interpreted as is customary in the art. It will be further understood that terms in common usage should also be interpreted as is customary in the relevant art and not in an idealised or overly formal sense unless expressly so defined herein.

One of ordinary skill in the art will appreciate the many possible applications and variations of the present invention based on the following examples of possible embodiments of the present invention.

Figure 1:
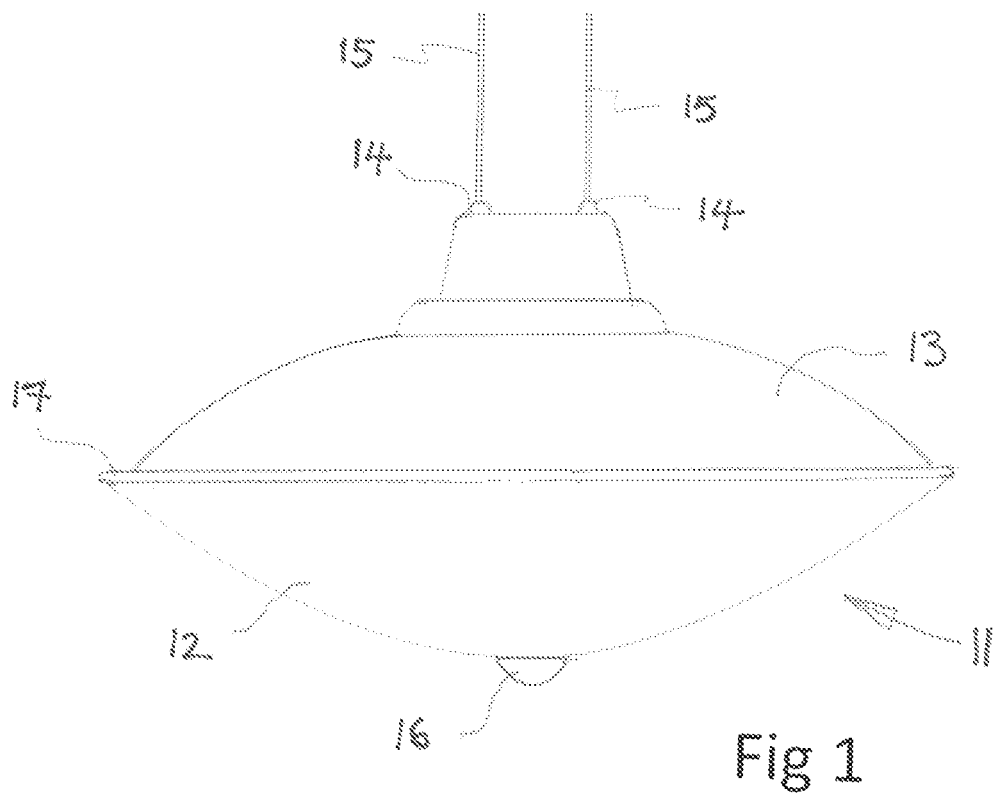
FIG. 1 is a side view of a luminaire formed as an embodiment of the invention.
Figure 2:
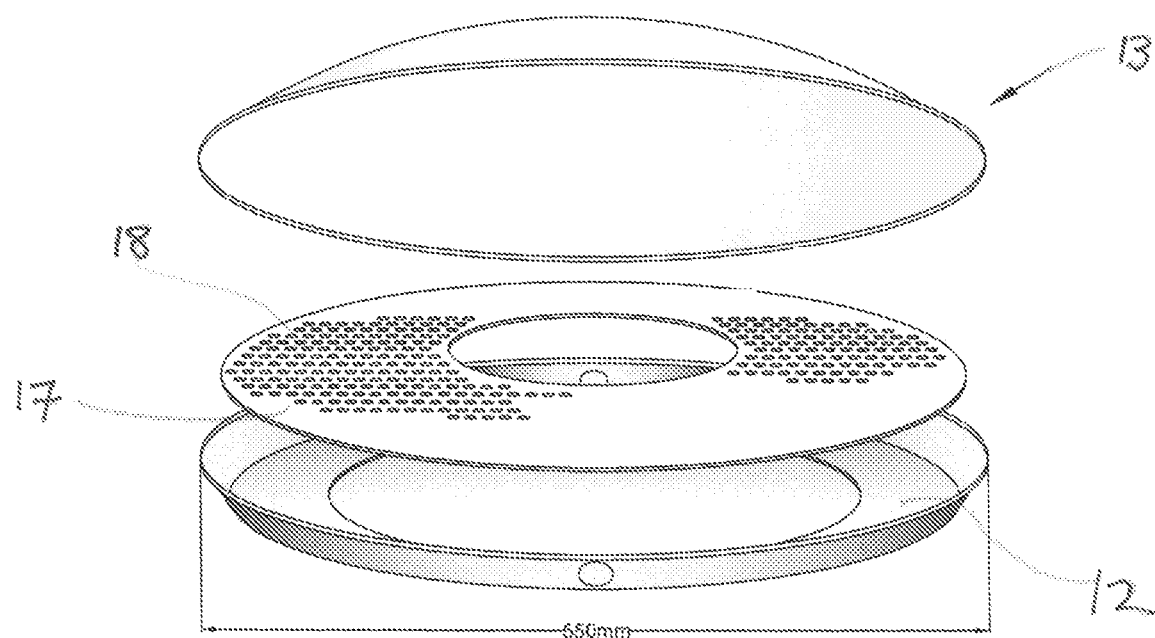
FIG. 2 is an exploded perspective view of the major components of the embodiment of FIG. 1.

Referring first to FIGS. 1 and 2, there is shown a luminaire, generally indicated 11 which comprises a base tray or mount 12 typically of polycarbonate, which has number of weakened portions (knockouts) for easy removal to allow the entry of supply wires and the fitting of component parts which will be described in more detail below. Secured around the perimeter of the base 11 is a fire-retardant polycarbonate diffuser 13 having attachment points or mounts 14 for suspension wires 15, which may also be the electrical supply lines for the luminaire. Other embodiments, not shown, may be formed for close fitting to the ceiling and would not have the wires 15, in which case the electrical supply lines may be introduced through a different part of the base or the diffuser.

Figure 3:
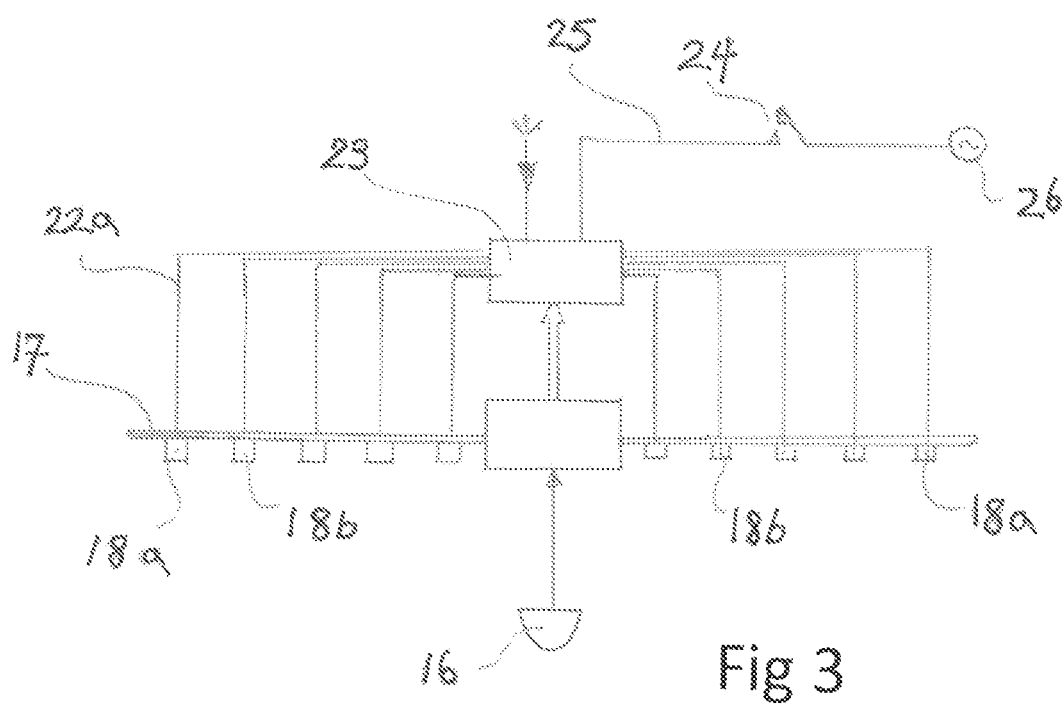
FIG. 3 is a schematic diagram illustrating the various parts of the luminaire shown in FIG. 1, which parts are not visible in FIG. 1.

Spanning between the base 12 and the diffuser 13 is located a lamp mount 17 in the form of a circular panel on which are mounted a number of light-emitting diodes (LEDs) 18 in two sets intercalated with one another and indicated 18a and 18b. The LEDs of set 18a have a 2700K colour temperature and comprise 30% of the total, whilst the LEDs of set 18b have a colour temperature of 6500K and comprise 70% of the total. The two sets of LEDs 18a and 18b are connected, as shown in FIG. 3, to a control unit 23 via respective sets of lines 22a and 22b. The LEDs 18a and 18b are distributed evenly over the surface of the lamp mount panel 17 to achieve maximum uniformity of illumination when selectively energised by the control unit 23 to provide a desired overall colour temperature of emitted light whereby to provide tuneable white light at a sufficient output to beneficially affect the circadian rhythm of an occupant in the illuminated environment in which the luminaire is fitted, typically a room in care home or the like.

The control unit 23 may be a Bluetooth module connected to receive signals from a sensor unit 16 which has a 360 degree sensitivity range and includes acoustic sensors and/or thermal sensors and/or optical (movement) sensors able to provide discreet monitoring of the occupant's physical activity, well-being and movement patterns within the room. Power to the control unit 23 is delivered from a power supply 26 along supply line 25 in which there is located a kinetic switch 24 operable by the room's occupant (the user) to provide a sense of control and autonomy in the illumination regime provided by the luminaire. This, however, does not affect the programme of lighting determined by the control unit from its stored programme as modified by signals from the sensor unit 16 in dependence on its monitoring of the activity (or otherwise) of the room's occupant. The control unit may also receive signals via Bluetooth protocol from the mesh network to vary the operation of the luminaire from that determined by the stored programme. The control unit 23 can also deliver signals via Bluetooth (for example Casambi Bluetooth) to a central location (not shown) for data harvesting based on the signals received from the array of sensors in the sensor unit 16 concerning the occupant's physical condition and movements, allowing remote monitoring by supervising staff.

Figure 4:
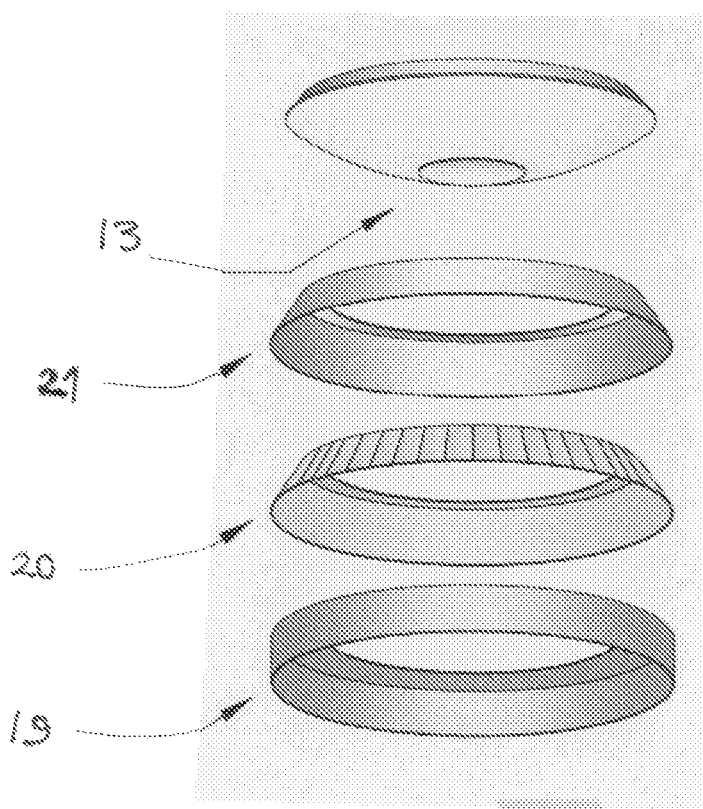
FIG. 4 illustrates various alternative components of the luminaire of the invention.

The luminaire may be fitted with one or more of a range of shade accessories as shown in FIG. 4, to provide a variation of appearance without affecting the performance of the luminaire. These may include a translucent polycarbonate shade 21, which may be in one of a number of different colours, or a pleated shade 20 serving as an additional diffuser for decorative effect. This makes it possible to create varied identities for different living spaces. Again, these may be in one of a variety of different colours. FIG. 4 also illustrates an optional translucent polycarbonate drum style accessory for a more contemporary appearance.

The present inventions can be embodied in other specific apparatus and/or methods. The described embodiments are to be considered in all respects as illustrative and not restrictive. In particular, the scope of the invention is indicated by the appended claims rather than by the description and figures herein. All changes that come within the meaning and range of equivalency of the claims are to be embraced within their scope.

The invention claimed is:

1. A biodynamic luminaire comprising a light source to provide an illumination output and which, in use, at least to some extent mitigates the detrimental effect of artificial lighting on an individual subject in an illuminated environment, the luminaire comprises one or more integral sensors which detect or determine one or more behaviors and/or one or more psychological states of the individual subject, and a control unit which changes the illumination output based on data received from or by the one or more integral sensors, in which the luminaire comprises a first set and a second set of light-emitting diodes (LEDs), in which the first and second LED sets have a different colour temperature, and in which the LEDs are selectively energisable by the control unit to provide a desired overall colour temperature of emitted light whereby, in use, to provide tuneable white light at a sufficient output to beneficially affect the individual subject's circadian rhythm in the illuminated environment.

2. The luminaire of claim 1, in which the one or more integral sensors are operable to detect or determine one or more variable environmental properties selected from: temperature, humidity, carbon dioxide level, carbon monoxide level, ambient noise level.

3. The luminaire of claim 1, in which the one or more integral sensors are operable to detect or determine one of more variable properties of the individual subject selected from: movement of the subject, body temperature, posture, heart rate, skin colour (pallor), stress level indicators, eye movement, sleep pattern, activity level.

4. The luminaire of claim 1, in which a variable property of the output illumination of the luminaire is the light intensity.

5. The luminaire of claim 1, comprising a plurality of sets of individual light sources of different properties, and control means is provided for selectively energising the light sources of different sets to achieve a target property of the output illumination.

6. The luminaire of claim 1, comprising a base tray and a diffuser, and between the base tray and the diffuser is a lamp mount on which are mounted two or more light-emitting diodes (LEDs), the LEDs are connected to the control unit.

7. The luminaire of claim 6, further comprising a sensor unit.

8. The luminaire of claim 6, in which the LEDs are distributed evenly over the surface of the lamp mount.

9. The luminaire of claim 7, in which the sensor unit has a 360-degree sensitivity range.

10. The luminaire of claim 7, in which the one or more integral sensors unit includes acoustic sensors and/or thermal sensors and/or movement sensors able to provide discreet monitoring of the individual subject's physical activity, well-being and movement patterns.

11. The luminaire of claim 7, in which the control unit can deliver information to a remote location for data harvesting based on signals received from the one or more integral sensors, allowing remote monitoring by supervising staff.

12. The luminaire of claim 6, in which the lamp mount is in the form of a generally circular panel.

13. The luminaire of claim 1, in which the first set of LEDs have a color temperature of approximately 2700K and the second set of LEDs have a color temperature of approximately 6500K.

14. The luminaire of claim 1, in which the first set of LEDs comprise approximately 30% of the total number of LEDs and the second set of LEDs comprise approximately 70% of the total number of LEDs.

15. The luminaire of claim 6, in which the luminaire is fitted with one or more shade accessories to provide a variation of appearance without affecting performance.

16. The luminaire of claim 1, in which the one or more integral sensors are based on millimetre wave technology.

17. The luminaire of claim 1, in which data is transmitted and/or received between the luminaire and a remote processor.

18. A care home or nursing home fitted with the luminaire of claim 1.

* * * * *